United States Patent [19]

Hill et al.

[11] Patent Number: 4,997,981

[45] Date of Patent: Mar. 5, 1991

[54] PROCESSES FOR 2-(1-PENTYL-3-GUANIDINO)-4-(2-METHYL-4-IMIDAZOLYL) THIAZOLE AND ANALOGS

[75] Inventors: Paul D. Hill, Groton; William M. Snyder, New London; Stanley W. Walinsky, Mystic, all of Conn.

[73] Assignee: Pfizer Inc., New York, N.Y.

[21] Appl. No.: 424,300

[22] PCT Filed: Oct. 29, 1986

[86] PCT No.: PCT/US86/02308

§ 371 Date: Apr. 20, 1989

§ 102(e) Date: Apr. 20, 1989

[87] PCT Pub. No.: WO88/03141

PCT Pub. Date: May 5, 1988

[51] Int. Cl.$^5$ ............................................. C07C 335/28
[52] U.S. Cl. ...................................... 564/30; 548/198; 564/27
[58] Field of Search ...................... 564/27, 30; 548/198

[56] References Cited

U.S. PATENT DOCUMENTS

| 4,234,735 | 11/1980 | Jones et al. | 548/198 |
| 4,262,122 | 4/1981 | Lees | 544/330 |
| 4,427,685 | 1/1984 | Stemp | 424/267 |
| 4,560,690 | 12/1985 | Reiter | 514/256 |

FOREIGN PATENT DOCUMENTS 1518230 10/1972 Fed. Rep. of Germany ...... 564/237

OTHER PUBLICATIONS

Wegard, "Preparative Organic Chemistry" 3rd ed., 1985, John Wiley (New York), pp. 540, 541.
March, "Advanced Organic Chemistry" 3rd ed., 1985, John Wiley (New York), pp. 315 and 371–377.

*Primary Examiner*—Robert Gerstl
*Attorney, Agent, or Firm*—Peter C. Richardson; J. Trevor Lumb; Robert K. Blackwood

[57] ABSTRACT

An amine substituion process for 2-(1-pentyl-3-guanidino)-4-(2-methyl-4-imidazolyl)thiazole, for precursor N-(pentylamidino)thiourea, and for analogs thereof of said compounds.

5 Claims, No Drawings 4,997,981

1

PROCESSES FOR 2-(1-PENTYL-3-GUANIDINO)-4-(2-METHYL-4-IMIDAZOLYL) THIAZOLE AND ANALOGS

BACKGROUND OF THE INVENTION

The present invention is directed to advantageous processes for the preparation of 2-(1-pentyl-3-guanidino)-4-(2-methyl-4-imidazolyl)thiazole and analogs, and to a crystalline, hydrated dihydrochloride salt thereof having advantageous properties.

Reiter, U.S. Pat. No. 4,560,690 has described 2-(1-pentyl-3-guanidino)-4-(2-methyl-4-imidazolyl)thiazole and various analogs, compounds having valuable antiulcer activity. That patent, which further details pharmaceutical compositions and a method of inhibiting ulcers with these compounds, is included herein by reference.

Reiter prepared the subject compounds via the following reaction scheme:

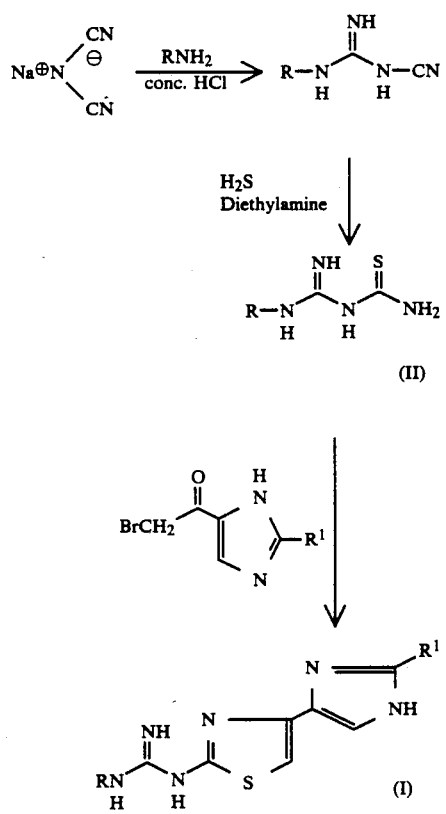

wherein R is benzyl or $(C_1-C_5)$alkyl and $R^1$ is $(C_1-C_5)$alkyl. The products were generally isolated as their dihydrobromide salts and converted to preferred dihydrochloride salts via their free base forms. This route employs toxic reagents, sodium dicyanamide and hydrogen sulfide, presenting environmental problems. In particular, the use of large excesses of hydrogen sulfide (or alternatively hydrogen sulfide under pressure) presents particular problems which limit batch sizes. This old scheme further lacks flexibility, it being necessary to carry out the entire sequence for each compound of the formula (I) that is desired.

2

SUMMARY OF THE INVENTION

The present invention is directed to highly flexible routes to compounds of the formula (I) which avoid toxic sodium dicyanimide and hydrogen sulfide, and employ an unprecedented acid catalyzed amine exchange reaction, carried out by action of an amine $RNH_2$ either on a 2-guanidino-4-(2-alkyl-4-imidazolyl)-thiazole, of the formula

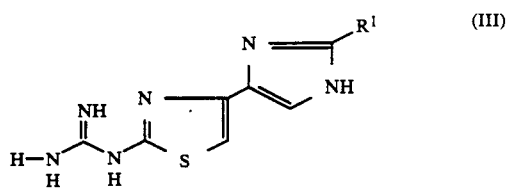

directly forming the compound of the formula (I), as defined above; or on an amidinothiourea

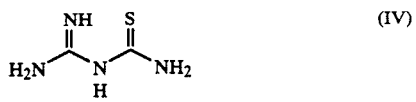

to form the N-substituted aminothiourea of the formula (II), as defined above; neat or in the presence of a reaction-inert solvent.

In one of the preferred embodiments of the present invention, an acid salt of (III), e.g., the dihydrochloride, is reacted with at least one molar equivalent of the amine neat or in the presence of a reaction-inert solvent or solvents (preferably in an excess of the amine) to directly form the corresponding acid salt of (I).

In a second preferred embodiment of the present invention, amidinothiourea is reacted with at least one molar equivalent of the amine $RNH_2$ in a reaction-inert solvent such as a lower alkanol in the presence of a molar excess of an acid, conveniently acetic acid.

The expression "reaction-inert solvent" refers to a solvent which does not interact with starting materials, intermediates or products in a manner which adversely affects the yield of the desired product $(C_1-C_5)$Alkyl refers to straight chain or branched alkyl groups containing from 1 to 5 carbon atoms. The preferred value of $R^1$ is methyl; the preferred values of R are benzyl, pentyl and 2-methylbutyl.

The present invention is also directed to crystalline 2-(1-pentyl-3-guanidino-4-imidazolyl)thiazole dihydrochloride trihydrate, having distinct advantages over the prior anhydrous dihydrochloride of Reiter, which is amorphous, less readily purified, and possesses properties which are generally less suitable for formulation and use as a medicinal agent in man.

DETAILED DESCRIPTION OF THE INVENTION

The processes of the present invention are readily carried out. When the product is directly the guanylthiazole derivative (I), the reaction is conveniently carried out employing an isolated mono or diacid salt of the compound (III), thus providing the source of the required acid catalyst. The acid catalyst can be a strong acid (e.g. HBr, HCl, $pCH_3C_6H_4SO_3H$) or a weak acid (e.g. $CH_3COOH$, $NH_4Cl$). It is most preferred to use the dihydrochloride salt of (III). The salt is heated with at least one molar equivalent of the amine RNH$_2$. The temperature which is generally well above ambient temperature, is not a critical feature of the present invention, temperatures in the range of 50°–150° C. being generally satisfactory, the preferred range being 95°–115° C. At temperatures which are above the boiling point of the amine, it will be necessary to carry out the reaction under pressure. The reaction is optionally carried out in the presence of a reaction-inert solvent as diluent, but it is preferred to simply carry out the reaction neat, in the presence of an excess of the amine (e.g. 5–20 molar equivalents).

The starting compounds (III), are conveniently prepared according to LaMattina et al. U.S. Pat. No. 4,374,843. When R$^1$ is methyl, LaMattina et al. reported isolation of the compound (III) as its monohydrobromide salt. The latter is better prepared as its dihydrobromide salt according to Cue, European Patent Application 178,123, published April, 1986. The latter is readily converted via its free base form to other acid salts, such as the presently preferred dihydrochloride salt.

When the product of the present process is the intermediate N-substituted guanylthiourea derivative (II), the amine exchange reaction is carried out under substantially identical conditions, although preferably at temperatures lower in the generally satisfactory range noted above (e.g. 50°–90° C.), conveniently on the commercially available "free base" form of the guanylurea (IV) in the presence of at least one molar equivalent each of the amine RNH$_2$ and of the acid (conveniently acetic acid), preferably in the presence of a reaction inert solvent, such as ethanol, as diluent.

The present amine exchange reactions are conveniently monitored by standard methods of TLC (thin layer chromatography) and HPLC (high performance liquid chromatography). The intermediates (II) are converted to the guanylthiazole derivatives according to the methods of Reiter, schematically represented above.

The present crystalline 2-(1-pentyl-3-guanidino)-4-(2-methyl-4-imidazolyl)thiazole dihydrochloride trihydrate is obtained by crystallization from dilute aqueous hydrochloric acid, optionally diluted with a water miscible organic solvent such as acetonitrile, at temperatures generally in the range of 0°–50° C. If desired, it is recrystallized from aqueous solvents (e.g., water/acetonitrile) in the same temperature range. At temperatures below 50° C. and ambient pressures, the trihydrate is stable, remaining in the crystalline trihydrate form. At temperatures above 50° C. (e.g. at 70° C. and ambient pressure) it slowly loses the water of hydration, but will readily regain water on storage at ambient temperature and high relative humidity. The trihydrate shows a characteristic strong endotherm at 107°–109° C. in differential scanning calorimetry.

The following examples are given by way of illustration and are not to be construed as limitation of this invention, many variations of which are possible within the scope and spirit thereof.

EXAMPLE 1

2-(1-Pentyl-3-guanidino)-4-(2-methyl-4-imidazolyl)-thiazole Dihydrochloride Trihydrate

Method A

To a 50 ml., 3-neck round bottom flask, equipped with reflux condenser, thermometer and mechanical stirrer was added pentylamine (15.0 g., 172 mmol) and 2-guanidino-4-(2-methyl-4-imidazolyl)thiazole dihydrochloride (10.0 g., 23.8 mmol). The thick slurry was heated to reflux (104° C.) under nitrogen, and at approximately 90° C. the reaction mixture became homogeneous. The reaction was heated at reflux for 19 hours. TLC and HPLC assays indicated that the reaction was complete The thick brown syrup was cooled to 50° C. and then 130 ml. of acetone was added followed by 12 ml. of concentrated HCl. Solids started to precipitate. The slurry was cooled to room temperature and granulated for 1 hour. The off-white solids were filtered, washed with acetone, and then air-dried at ambient temperature. The crude dried solid weighed 6.93 g. (48.8% yield).

The crude product was dissolved in 80 ml. of warm (45° C.) acetone/water (1:1) and then treated with 1.0 gram of activated carbon. The carbon-treated solution was filtered through a funnel precoated with diatomaceous earth, and then the filter pad was washed with 11 ml. of acetone/water (1:1). The filtrate was transferred to a clean flask and cooled in an ice bath. Concentrated HCl (32 ml.) was added slowly. Solids precipitated after approximately 20% of the concentrated acid was added. Once the acid addition was completed, the solids were granulated for 1.0 hour at ambient temperature. The white solid was filtered, washed with acetone and then air-dried to afford crystalline trihydrate dihydrochloride salt (5.85 g., 1.5% overall yield). Microscopic examination under a polarizing microscope showed needle-like crystals. Differential scanning showed a major endotherm at 107°–109° C., unchanged on vacuum drying without heat.

Anal Calcd. for $C_{13}H_{20}N_6S.(HCl)_2.(H_2O)_3$: C, 37.22; H, 6.74; N, 20.04; S, 7.64; Cl$^-$, 16.90; H$_2$O, 12.87.

Found: C, 36.97; H, 6.57; N, 19.89; S, 7.82; Cl$^-$, 16.83; H$_2$O, 13.32.

On storage at temperatures above 50° C. the product loses water. For example, after one week at 70° C., the water level was reduced to 5.69%. On reequilibration at room temperature and 84% relative humidity for two weeks, the trihydrate reformed.

Anal. Found: C, 37.02; H, 6.66; N, 19.83; H$_2$O, 13.45.

On vacuum drying at 65° C. to constant weight, microscopic examination indicated the resulting anhydrous product to be amorphous. Differential scanning calorimetry no longer showed the 107°–109° C. endotherm.

HPLC analyses were conducted on a microBONDAPAK C$_{18}$ column (7.8 mm ID×30 cm) using UV detector (254 nm). An eluant containing aqueous buffer and methanol (1:1) was used at 1 ml/min. The buffer contained 0.05M KH$_2$PO$_4$, 0.01M Na hexanesulfonate and 0.1% triethylamine which was adjusted to pH 3.0 with phosphoric acid.

TLC analyses were conducted on Merck Pre-Coated silica gel plates (60F-254) using a methanol/water/diethylamine eluant (20:4:1).

Variation in stoichiometry, reaction time and temperature led to the following results:

| Variables | | | | Overall Yields | |
|---|---|---|---|---|---|
| Molar Equiv. Amine | Acid (Molar Equiv.) | Temp. (°C.) | Time (hrs.) | Crude (%) | Recryst. (%) |
| 5.1 | HCl (2.0) | 104 | 19 | 48 | — |
| 10.0 | HCl (2.0) | 102 | 24 | 38 | 32 |

-continued

| Variables | | | | Overall Yields | |
|---|---|---|---|---|---|
| Molar Equiv. Amine | Acid (Molar Equiv.) | Temp. (°C.) | Time (hrs.) | Crude (%) | Recryst. (%) |
| 10.0 | HCl (2.0) | 102–107 | 19 | 48 | 43 |
| 17.6 | HCl (2.0) | 103 | 17.5 | 43 | — |
| 13.4 | HOAc[a] (1.0) | 104 | 32 | 60 | — |
| 13.4 | PTS[b] (1.0) | 104 | 18 | 61[c] | — |

[a] acetic acid
[b] p-toluenesulfonic acid
[c] by HPLC assay

Method B

The amorphous dihydrochloride of 2-(1-pentyl-3-guanidino)-4-(2-methyl-4-imidazolyl)thiazole was prepared according to Example 5 of U.S. Pat. No. 4,560,690. Thus 8.1 g. of the dihydrobromide salt was dissolved in 150 ml. of $H_2O$ at 50° C. $Na_2CO_3.H_2O$ (8.86 g.) in 80 ml. $H_2O$ was added over 1 hour with stirring. After stirring for an additional 0.5 hour at ambient temperature, the base was recovered by filtration and incompletely dried for 48 hours in vacuo. The entire batch was taken into 200 ml. acetone, clarified by filtration and the filtrate acidified with 3.4 ml. 12N HCl and diluted with 100 ml fresh acetone. Recovery by filtration and drying at 60° in vacuo for 24 hours gave 6.3 g. of amorphous dihydrochloride correctly analyzing for $C_{13}H_{20}N_6S.(HCl)_2.0.5H_2O$: Calcd.: C, 41.71; H, 6.19; N, 22.45. Found: C, 41.90, 41.60; H, 6.20, 6.23; N, 22.55, 22.48. This product (3.01 g.) was dissolved in 75 ml. $H_2O$ with stirring. Activated carbon, 0.3 g., was added and the mixture stirred for 15 minutes and then filtered. Concentrated HCl (25 ml.) was added to the filtrate. Crystallization began within a few minutes. After granulating for 1 hour, crystalline title product was recovered by filtration, with 4 ml. $H_2O$ wash, and air dried for 18 hours, 2.9 g.; water content 12.6%; physical properties as product of Method A. The product was optionally washed with a small amount of acetone, or repulped in 60 ml. of $CH_3CN$ for 2 hours and refiltered, in order to facilitate drying.

The product was optionally recrystallized by dissolving 3.4 g. of the trihydrate in 34 ml. of $H_2O$ by warming to 50° C. $CH_3CN$ (180 ml.) was added, maintaining 50° C. The mixture was cooled slowly with stirring to 20° C. Crystallization began at 32° C. The product was recovered as the trihydrate (water content 12.95%) having unchanged physical properties.

EXAMPLE 2

2-[1-(2-Methylbutyl)-3-guanidino]-4-(2-methyl-4-imidazolyl)thiazole

To a 500 ml., 3-necked round bottom flask was added racemic 2-methylbutylamine (125.0 g., 1.43 mol) and 2-guanidino-4-(2-methyl-4-imidazolyl)thiazole dihydrochloride (42.2 g., 0.143 mol). The mixture was heated to reflux (97° C.) and quickly afforded a purplish solution. The solution was heated for 19 hours at reflux by which time HPLC analysis showed that the reaction was complete. Volatiles were removed from the reaction by an atmospheric distillation and then the cooled concentrate (70° C.) was dissolved in 525 ml. of acetone. With good agitation, 50 ml. of conc. HCl was slowly added to afford a thick slurry (40° C.). The mixture was cooled to 25° C. and granulated for 2 hours. The solids were filtered, washed with 100 ml. of acetone and then air-dried at ambient temperature. Pinkish solids (36.5 g., 70% yield) were obtained The crude solid was dissolved in acetone (316 ml.) and water (316 ml.) and then 2.0 grams of activated carbon was added. After stirring for 10 minutes the mixture was filtered through diatomaceous earth to give a yellow filtrate. Concentrated HCl was slowly added to the filtrate to the haze point and then the mixture was stirred for 5 minutes to obtain a thick white slurry. The remainder of 173 ml. of conc. HCl was added and then the slurry was granulated for 1.5 hours at 25° C. The solids were filtered, washed with acetone, and then dried in vacuo overnight. White, crystalline trihydrate dihydrochloride was obtained (33.2 grams) in a 92% recrystallization yield.

EXAMPLE 3

2-(1-Benzyl-3-guanidino)-4-(2-methyl-4-imidazolyl)-thiazole

By the method of the preceding Example, using a reaction time of 2 hours at 110° C., benzylamine and 2-guanidino-4-(2-methyl-4-imidazolyl)thiazole dihydrochloride were converted to crude title product in 26–44% yield by HPLC assay.

EXAMPLE 4

N-(Pentylamidino)thiourea

To a one liter, 3-necked round bottom flask which was equipped with a mechanical stirrer, thermometer, and reflux condenser were added absolute ethanol (180 ml.) and pentylamine (100.0 g., 1.15 mol). The amine solution was cooled in an ice bath while glacial acetic acid (68.9 g., 1.15 mol) was slowly added. Amidinothiourea (90.37 g., 0.76 mol) was added and then the mixture was heated to reflux (85° C.). After 24 hours at reflux, HPLC analysis of the reaction solution indicated that title product (72.6 area %) had formed and that residual amidinothiourea (8.5 area %) remained.

Hot water (750 ml.) was added to the amber solution. After filtration, the solution was slowly cooled to room temperature. A thick, white slurry formed and was granulated for 30 minutes at ambient temperature. The solid was filtered, washed with water (50 ml.) followed by hexane (150 ml.) and then air dried. Crude title product was obtained in approximately 50% yield as the partial acetate salt.

The crude product was dissolved in ethyl acetate (500 ml.) and then washed with 5% $NaHCO_3$ solution (2×100 ml.). The ethyl acetate layer was dried and then heated to reflux. Cyclohexane (700 ml.) was added and the solution was allowed to cool to room temperature. The solids were filtered, washed with cyclohexane and then air dried. Purified title product was isolated as a sharp melting solid; m.p. 102°–104° C.

The reaction was repeated, varying the proportion of reagents, acid catalyst, solvent reaction time and temperature with the following results:

| Variables | | | | | Yield | |
|---|---|---|---|---|---|---|
| Molar Equiv. Amine | Acid (Molar Equiv.) | Solvent | Time (hr.) | Temp. (°C.) | HPLC Assay | Isolated |
| 1.5 | HOAc[a] (1.5) | EtOH[b] | 67 | 85 | 73 | 48 |
| 1.4 | HOAc[a] (2.0) | EtOH[b] | 60 | 87 | 67 | 58 |
| 1.0 | HOAc[a] | IPO[c] | 49 | 70 | 51 | — |

-continued

| Variables | | | | | Yield | |
|---|---|---|---|---|---|---|
| Molar Equiv. Amine | Acid (Molar Equiv.) | Solvent | Time (hr.) | Temp. (°C.) | HPLC Assay | Isolated |
| 5.0 | (1.0) NH₄Cl (2.0) | IPO^c | 55 | 50 | 34 | — |

^a acetic acid
^b ethanol
^c isopropanol

EXAMPLE 5

Capsule Containing 100 mgA of 2-(1-pentyl-3-guanidino)-4-(2-methyl-4-imidazolyl)-thiazole

Method A

The following materials were thoroughly blended in the indicated proportions by weight:

| | |
|---|---|
| 2-(1-pentyl-3-guanidino)-4-(2-methyl-4-imidazolyl)thiazole dihydrochloride trihydrate | 144.9* |
| lactose, anhydrous | 173.8 |
| starch 1500 | 173.8 |
| magnesium stearate | 7.5 |

*144.9 mg. of dihydrochloride trihydrate is equivalent to 100 mg. of anhydrous free base, i.e., 100 mgA (100 mg. of activity).

Hard gelatin capsules of suitable size were filled with 500 mg. each of this blend to form containing 100 mgA/capsule. These capsules showed good chemical and physical stability after storage under challenge conditions (96% drug released in 15 minutes in water using standard dissolution methods).

Capsules containing 50 mgA are analogously prepared using 500 mg of a blend composed of 72.5 parts by weight of dihydrochloride trihydrate, 211.2 parts by weight of each of anhydrous lactose and starch 1500, and 5.1 parts by weight of magnesium stearate.

We claim:

1. A process for the preparation of a compound of the formula

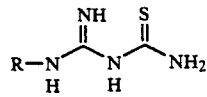

or an acid addition salt thereof, wherein R is benzyl or (C₁-C₅)alkyl, which comprises heating amidinothiourea of the formula

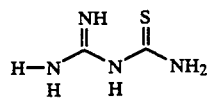

and an acid catalyst, or an acid addition salt of said amidinothiourea, with at least one molar equivalent of an amine of the formula

RNH₂ neat or in a reaction-inert solvent.

2. A process of claim 1 wherein R is pentyl.
3. A process of claim 1 which employs said amidinothiourea and at least one molar equivalent of acetic acid or ammonium chloride as the acid catalyst in a lower alkanol.
4. A process of claim 3 wherein R is pentyl.
5. The process of claim 4 wherein the acid catalyst is acetic acid and the solvent is ethanol.

* * * * *

UNITED STATES PATENT AND TRADEMARK OFFICE
CERTIFICATE OF CORRECTION

PATENT NO. : 4,997,981

DATED : March 5, 1991

INVENTOR(S) : Paul D. Hill, William M. Snyder and Stephen W. Walinsky

It is certified that error appears in the above-identified patent and that said Letters Patent is hereby corrected as shown below:

At column 2, line 51 directly after "guanidino", insert -- )-4-(2-methyl --.

Signed and Sealed this

Thirtieth Day of March, 1993

Attest:

STEPHEN G. KUNIN

Attesting Officer

Acting Commissioner of Patents and Trademarks